US00PP28272P3

(12) United States Plant Patent
Fraser

(10) Patent No.: US PP28,272 P3
(45) Date of Patent: Aug. 15, 2017

(54) ***COPROSMA* PLANT NAMED 'GOLDEN STAR'**

(50) Latin Name: *Coprosma repens*
Varietal Denomination: Golden star

(71) Applicant: Peter John Fraser, Waikato (NZ)

(72) Inventor: Peter John Fraser, Waikato (NZ)

( * ) Notice: Subject to any disclaimer, the term of this patent is extended or adjusted under 35 U.S.C. 154(b) by 114 days.

(21) Appl. No.: 14/756,776

(22) Filed: Oct. 10, 2015

(65) Prior Publication Data

US 2017/0105326 P1 Apr. 13, 2017

(51) Int. Cl.
*A01H 5/02* (2006.01)

(52) U.S. Cl.
USPC ..... Plt./226

(58) Field of Classification Search
USPC ..... Plt./226
See application file for complete search history.

(56) References Cited

PUBLICATIONS

UPOV hit on *Coprosma* plant named 'Golden Star', NZ PBR SHM360, published Oct. 9, 2015.*

* cited by examiner

*Primary Examiner* — Anne Grunberg

(57) ABSTRACT

A new cultivar of *Coprosma* plant named 'Golden Star' that is characterized by a compact habit and variegated yellow leaves with an irregular green center and orange margins.

1 Drawing Sheet

Botanical classification: *Coprosma repens.*
Variety denomination: 'Golden Star'.

BACKGROUND OF THE INVENTION

The present invention relates to a new and distinct cultivar of *Coprosma* plant botanically known as *Coprosma repens* and hereinafter referred to by the cultivar name 'Golden Star'.

The new cultivar was discovered by the inventor in a cultivated area of Kihikihi, New Zealand in 2011. 'Golden Star' was discovered as a naturally occurring branch mutation of *Coprosma* 'Evening Glow' (not patented).

Asexual reproduction by tip cuttings of the new cultivar 'Golden Star' was first performed in 2013 in Kihikihi, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Coprosma* cultivar 'Golden Star'.

1. *Coprosma* 'Golden Star' exhibits a compact habit.
2. *Coprosma* 'Golden Star' exhibits variegated yellow leaves with an irregular green center and orange margins.

The closest comparison cultivars are the parent plant *Coprosma* 'Evening Glow' (not patented) and 'Ignite' (not patented). The new cultivar 'Golden Star' is distinguishable from 'Evening Glow' by the following characteristics:

1. 'Golden Star' has variegated yellow leaves with an irregular green center and orange margins. The leaves of 'Evening Glow' are green with yellow-green center blotches and red margins.

The new cultivar 'Golden Star' is distinguishable from 'Ignite' by the following characteristics:

1. 'Golden Star' has variegated yellow leaves with an irregular green center and orange margins. The leaves of 'Ignite' are brown with green center blotches and red margins.

BRIEF DESCRIPTION OF THE DRAWING

The accompanying photograph illustrates the distinguishing traits of *Coprosma* 'Golden Star'. The plant in the photograph shows an overall view of a 12 month old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Coprosma* cultivar named 'Golden Star'. Data was collected in Cambridge, New Zealand from 12 month old outdoor grown plants in 2.5 liter containers. The time of year was Fall in the Southern Hemisphere and the average temperature range was 10 to 25 degrees Centigrade during the day and 5 to 12 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Golden Star' has not been tested under all possible conditions and phenotypic differences may be observed with variations in environmental, climatic, and cultural conditions, however, without any variance in genotype.

Botanical classification: *Coprosma repens* 'Golden Star'.

Use: Ornamental perennial.
Parentage: 'Golden Star' is a naturally occurring branch mutation of *Coprosma* 'Evening Glow'.
Vigor: Moderate.
Growth rate: Moderate.
Growth habit: Freely branching, dense, bushy habit.
Plant shape: Broad upright inverted triangle.
Suitable container size: 2.5 liter container.
Height: Average 70-91 cm. in height.
Width: Average 70-91 cm. in width.
Low temperature tolerance: 2 degrees Centigrade.
High temperature tolerance: 38 degrees Centigrade.
Propagation: Tip cuttings.
Time to initiate roots: Approximately 18 days in the Summer at 20 degrees Centigrade and 24 days in the Winter at 20 degrees Centigrade.
Time to produce a rooted cutting: Approximately 90 days in the Summer at 20 degrees Centigrade and 90 days in the Winter at 15 degrees Centigrade.
Root system: Fine and fibrous.
Lateral branches:
*Quantity.*—Approximately 28.
*Dimensions.*—30 cm. in length and 3.2 mm. in diameter.
*Internode length.*—7 mm.
*Stem color.*—176B.
*Strength.*—Strong.
*Pinching.*—Yes, at 50 days.
Foliage:
*Texture.*—Smooth, glossy.
*Leaf arrangement.*—Opposite.
*Leaf attachment.*—Sessile.
*Compound or single.*—Single.
*Leaf shape.*—Obovate.
*Leaf apex.*—Obtuse.
*Leaf base.*—Rounded.
*Leaf length.*—Average 2.4 cm. in length.
*Leaf width.*—Average 1.4 cm. in width.
*Pubescence.*—Absent.
*Leaf margin.*—Entire, unevenly recurved, slightly wavy.
*Vein pattern.*—Pinnate.
*Young leaf color* (*upper surface*).—1C, irregular center 141B.
*Young leaf color* (*lower surface*).—Center 4B, irregular margins 144C.
*Mature leaf color* (*upper surface*).—1C, irregular center 141B, margins 187B.
*Mature leaf color* (*lower surface*).—Center N34C, irregular margins 197B.
*Durability of foliage to stress.*—Moderate to high.
Flowers: *Coprosma* 'Golden Star' has not produced flowers to date.
Disease and insect resistance: Plants of the new *Coprosma* have not been observed for disease or insect resistance.

The invention claimed is:

1. A new and distinct variety of *Coprosma* plant named 'Golden Star' as described and illustrated.

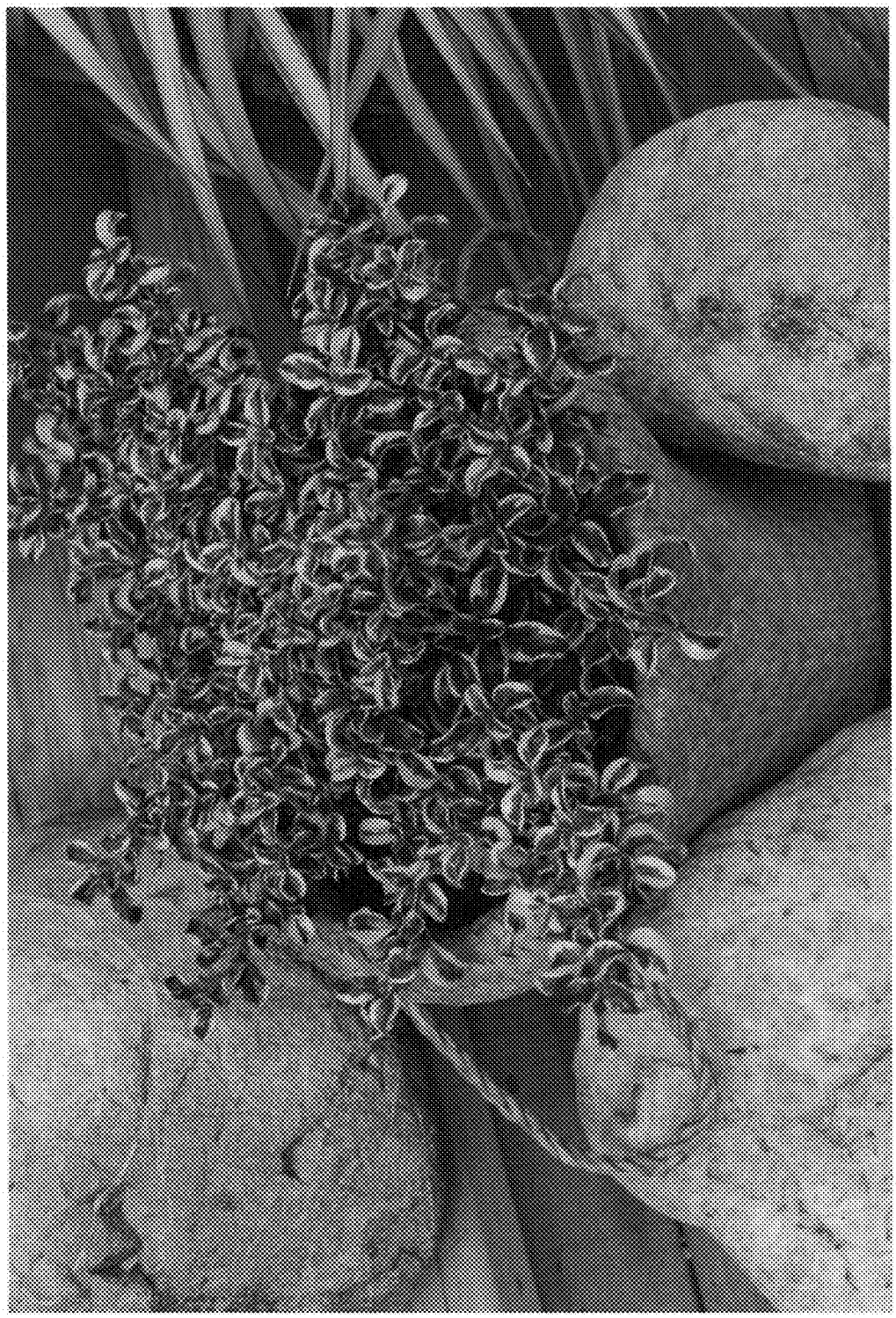

* * * * *